United States Patent [19]

Richard et al.

[11] Patent Number: 5,795,719
[45] Date of Patent: Aug. 18, 1998

[54] BIOTINYLATED LATEX MICROSPHERE, PROCESS FOR THE PREPARATION OF SUCH A MICROSPHERE AND USE AS AGENT FOR BIOLOGICAL DETECTION

[75] Inventors: Joël Richard, Chantilly; Sophie Vaslin, Bry-sur-Marne; Pierre Blond, Francheville; Françoise Lerat, Mornant; Jean-Luc Taboureau, Chaponost, all of France

[73] Assignee: Societe Prolabo, Fontenay-Sousbois, France

[21] Appl. No.: 525,065

[22] Filed: Sep. 8, 1995

[30] Foreign Application Priority Data

Sep. 9, 1994 [FR] France .................. 94 10789

[51] Int. Cl.⁶ .................................................. C12Q 1/68
[52] U.S. Cl. .......................... 435/6; 435/7.1; 435/7.2; 435/810; 436/501; 536/22.1; 536/23.1; 536/24.1; 536/24.3; 536/24.31; 536/24.32; 536/25.4; 935/77; 935/78
[58] Field of Search ............... 435/5, 6, 7.1, 7.2, 435/810; 436/501; 536/22.1, 23.1, 24.1, 24.3–24.33, 25.4; 935/77,78

[56] References Cited

U.S. PATENT DOCUMENTS 5,374,516  12/1994  Sutton et al. ..................... 435/5

FOREIGN PATENT DOCUMENTS

| 0 138 297 | 4/1985 | European Pat. Off. |
| 0 154 788 | 9/1985 | European Pat. Off. |
| 0 302 715 | 8/1989 | European Pat. Off. |
| 0 591 809 | 4/1994 | European Pat. Off. |
| WO90/13815 | 11/1990 | WIPO |

*Primary Examiner*—Ardin H. Marschel
*Attorney, Agent, or Firm*—Jacobson, Price, Holman & Stern, PLLC

[57] ABSTRACT

The invention relates to a latex microsphere consisting of polymers obtained by polymerization of ethylenically unsaturated monomers, having functional groups at the surface, and remarkable in that biotinyl residues are grafted onto at least part of the said groups, via a divalent chain.

It also relates to the avidin- or streptavidin-biotin complex obtained with the aid of the said microsphere and to the use of the microsphere or of the complex as agent for diagnosis, for biological assay or for immunological assay.

35 Claims, No Drawings

BIOTINYLATED LATEX MICROSPHERE, PROCESS FOR THE PREPARATION OF SUCH A MICROSPHERE AND USE AS AGENT FOR BIOLOGICAL DETECTION

The present invention relates to a new biotinylated latex microsphere, to a biotinylated avidin or streptavidin-microsphere complex, to a process for the preparation of such a microsphere and to the application of the biotinylated latex microsphere or of the complex with avidin or streptavidin as agent for diagnosis or for biological (immunological, enzymatic, and the like) assay and in molecular biology.

The (strept)avidin-biotin interaction has been used for many years in various biological applications, especially in the field of separation and sequencing of DNA ( . . . ), of hybridization of nucleic acids, of immunological assays, of cell labelling and of cell sorting.

The advantages of the streptavidin-biotin or avidin-biotin recognition system are numerous and well known; they are:

the creation of a strong interaction between these two molecules, which ensures the stability of the complex under varying pH conditions during the different steps of washing, coupling and analysis, the reduction of nonspecific coupling, the relative ease of introduction of the biotin into the biological macromolecules without modifying their activity, for the purpose of the coupling to the streptavidin support.

Biotin, also called vitamin H, of formula:

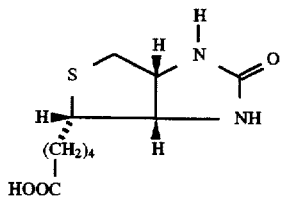

has the advantage of being able to bind, with a very high selectivity, to avidin or streptavidin (kd=$1.3 \times 10^{-15}$ mole/l)

Avidin is a glycoprotein present in egg white, which has four identical subunits of 128 amino acids each and an isoelectric point of 10. It can bind up to four molecules of biotin, that is to say one biotin per subunit. The term "avidin" is also intended to designate the nonglycosylated form of this protein which has essentially the same affinity characteristics as the glycosylated protein.

Streptavidin is a protein obtained from the culture of *Streptomyces avidinii*, which also has four identical subunits and an isoelectric point of about 5–6.

Usually, the streptavidin used has been subjected to digestion with proteinase K. However, within the framework of the present description, the expression "streptavidin" is also intended to designate the native form obtained for example after cloning of the streptavidin gene (Argarana CE, Nucleic Acids Res. 1986; 14:1871–1882).

Moreover, the application of latex microspheres as material for medical diagnosis is known. For example, latex particles are used in agglutination tests and are used to detect the presence or the absence of antibody or antigen. In concrete terms, an antibody or an antigen is bound to the surface of a latex particle which may subsequently react with the corresponding antigen(s) or antibody(antibodies) contained in a body fluid, for example blood serum, spinal fluid (SF), urine, or a preparation of tissue extract. The methods of detection are well known to persons skilled in the art.

Latexes have been recently proposed which contain magnetic microspheres having streptavidin groups at the surface and which are especially used in the field of medical diagnosis and immunological assay.

However, such a latex does not lead to a completely satisfactory result because the closeness of the surface of the particles may induce a partial denaturation of the streptavidin, which decreases its capacity to couple with biotin, or at least makes it less controllable.

The invention proposes a process for the preparation of biotinylated latex microspheres which ensure:

a) easy control of the covalent grafting of modified biotin, which opens the possibility of obtaining particles whose surface concentration of biotin is varied and known.

The invention also proposes new microspheres:

b) which offer the possibility of preparing, in any manner, from the same base, avidin latexes or streptavidin latexes: which makes it possible to propose to users two products of different added value. Streptavidin is more expensive, but it gives less interference than avidin because of its lower isoelectric point (close to 5–6) and because it normally lacks glycosylated residues which are present at the surface of each subunit in avidin.

c) which allow the elimination of steric stresses due to the closeness of the solid phase which the polymer support represents, d) which promote the formation of the biotin-streptavidin, or biotin-avidin complex, e) which make it possible to preserve the capacity to bind three biotinylated conjugates.

The invention relates, firstly, to a latex microsphere consisting of polymers obtained by polymerization of ethylenically unsaturated monomers, having functional groups at the surface, and characterized in that biotinyl residues are grafted onto at least part of the said groups, via a divalent chain.

The biotinylated residue/divalent chain combination is also called "biotinylated chain".

The latex microspheres conventionally consist of polymers obtained by polymerization of ethylenically unsaturated monomers and are functionalized at the surface.

They are homopolymers or copolymers containing units derived from vinylaromatic monomers, ethylene monomers, ethylenic or alkanoic acids or esters, of which a proportion is functionalized.

This type of polymer is easily accessible to any person skilled in the art and only few of them will be mentioned below, with no limitation being implied. They may be:

ethylene monomers of the isoprene, 1,3-butadiene, vinylidene chloride or acrylonitrile type, vinylaromatic monomers such as styrene, bromostyrene, alpha-methylstyrene, ethylstyrene, vinyltoluene, chlorostyrene or chloromethylstyrene or vinylnaphthalene, alkenoic acids, esters or anhydrides such as acrylic or methacrylic acids, alkyl acrylates and methacrylates, of which the alkyl group has 3 to 10 carbon atoms, hydroxyalkyl acrylates, acrylamides, esters of ethylenic acids containing 4 or 5 carbon atoms, as well as, difunctional monomers such as divinylbenzene or 2,2-dimethyl-1,3-propylene diacrylate and/or other water-insoluble copolymerizable monomers.

A portion of the monomers carries groups capable of reacting, directly or indirectly, with functional groups of for example the amine or carboxyl type, which are carried by biological molecules such as proteins and enzymes. As representatives of these functional groups, there may be mentioned halogens, carboxyl, amine, isocyanate, aziridine, aldehyde and sulphonyl groups, and epoxy and chloromethyl functional groups.

The monomers more particularly used within the framework of the present invention belong to the family of arylenes and/or alkylenes. They are preferably vinyl-aromatic compounds such as: styrene, alpha-methylstyrene, ethylstyrene, tert-butylstyrene and vinyltoluene. Preferably, these monomers are substituted with one or more functional groups of the halogen, amine, alkoxy, carboxyl and/or sulphonyl type.

These monomers are used alone or mixed with each other in any proportion.

The polymer particles can be obtained using any polymerization technique such as the conventional polymerization in emulsion, the polymerization in microemulsion, in suspension or in microsuspension, or, where appropriate, by polymerization in organic medium. These techniques, which are familiar to persons skilled in the art, will not be recalled here.

The particles according to the invention are hydrophobic and have preferably a size generally of between 0.01 and 20 microns and preferably less than 5 microns. They are sized, monodisperse and present in the latex in a quantity varying between 0.05 and 30% by weight of the total weight of the latex, preferably between 0.1 and 2%.

Generally, the surface density of functional groups per square nanometer of microsphere is between 0.1 and about 50.

The latex microspheres may be magnetizable and, in this case, they are combined with magnetizable materials as is for example described in U.S. Pat. Nos. 4,339,337, 4,358,388 and 4,948,739.

Among the materials capable of constituting the magnetizable parts of the microspheres, there may be mentioned magnetite, haematite, chromium dioxide, mixed oxides of yttrium-iron, ferrites such as manganese, nickel, manganese-zinc ferrites . . . . cobalt, nickel, gadolinium, samarium-cobalt alloys . . . The preferred materials are generally magnetite and haematite.

The quantity of magnetizable materials contained in the microspheres corresponds to about 0.5 to 70%, preferably to about 15 to 60% by weight of the magnetizable composite microsphere.

As a result of the presence of the divalent chain which acts as "spacer arm", the steric stresses due to the closeness of the solid phase which the microsphere represents are eliminated. Furthermore, the protein (avidin or streptavidin), being distant from the surface of the microsphere, preserves its capacity to bind three other biotinylated conjugates.

Preferably, the divalent chain has a mean length ranging from 5 to 120 Å, advantageously from 5 to 50 Å and more advantageously in the vicinity of 15 Å.

The expression "biotinyl residue" will be understood to mean a radical capable of being conjugated with avidin or streptavidin. This residue should contain the structure of formula:

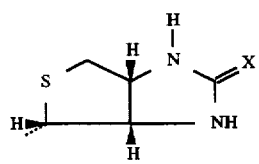

I in which:
X is either an oxygen atom, a sulphur atom or an imino radical N—H.

In general, this residue will consist of the biotinyl radical of formula:

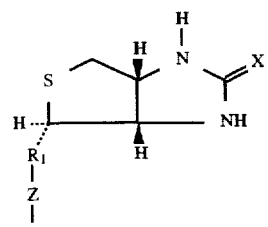

II in which:
$R_1$ is a divalent $C_1$-$C_8$ hydrocarbon radical
X is either an oxygen atom, a sulphur atom or an imino radical N—H,
Z is a group C=O or —S—

Preferably, the divalent chain contains 3 to 80 carbon atoms, advantageously 8 to 20.

It is generally an optionally substituted divalent hydrocarbon radical, optionally containing in the main chain one or more heteroatoms chosen from nitrogen, oxygen, sulphur or phosphorus atoms, one or more of the carbon atoms being possibly carbonyl groups or derivatives (imine, oxime and the like) or containing one or more rings or heterocycles.

The substituents of the divalent radical are those which do not produce steric hindrance such that the grafting onto the functional groups of the microsphere would become difficult or even impossible. They are therefore substituents of low bulkiness such as methyl, amino or OH radicals and the like.

Likewise, these substituents or the heteroatoms which are part of the chain itself must not interfere with the reaction between the terminal group of this chain and the functional groups.

Generally, the number of biotinylated chains on each latex microsphere must be sufficient in order to allow the carrying out of a diagnostic test.

From a practical point of view, this number is a greater or lesser proportion of the quantity of functional groups present on the microsphere.

This proportion varies advantageously between 1 and 50% of the functional groups present at the surface of the microsphere; preferably, the proportion is between 5 and 30%.

As indicated above, the surface density of functional groups per square nanometer of microspheres is between 1 and 50, the said number being easily determined.

According to a first variant, the latex microsphere has the following structure:

III in which:
n represents the mean number of molecules grafted per unit of surface area,
M represents the latex microsphere
B represents the biotinylated chain,
R is an optionally substituted divalent hydrocarbon radical optionally containing one or more hetero-atoms chosen from the nitrogen, oxygen, sulphur or phosphorus atoms, one or more carbonyl groups or derivatives, one or more rings or heterocycles.

Preferably, B corresponds to the formula II above where Z is C=O. Preferably still, $R_1$ is the divalent radical $(CH_2)_4$.

However, the invention is not limited to this specific form of biotinyl residue and may also extend to the residues whose

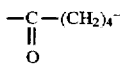

chain may be replaced with an equivalent chain.

Preferably, among the numerous divalent radicals R which may be suitable for the production of the microspheres according to the invention, there may be mentioned the divalent radical of cadaverine, ethylene-diamine, hexamethylenediamine or a dihydrazide such as adipodihydrazide, a peptide residue, a basic amino acid residue such as lysine, preferably a residue of formula:

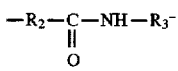

in which $R_2$, $R_3$, which are identical or different, are a divalent $C_1$–$C_8$ preferably $C_2$–$C_6$, advantageously $C_5$ chain.

It has already been indicated that the surface density of the functional groups at the surface of the microsphere was advantageously between 1 and 50 per square nanometer.

Preferably, the percentage of biotinylated spacer arms grafted on the surface functional groups is between 1 and 50%. Advantageously, the percentage is between 5 and 30%.

The number n can therefore be determined given the diameter of the sphere and is generally between about 0.1 and about 10.

According to a second variant, the latex microsphere has the following structure:

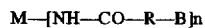   IV in which M, n have the same meaning as in the structure III, B represents the biotinylated chain R represents an optionally substituted divalent hydrocarbon radical optionally containing one or more heteroatoms chosen from the nitrogen, oxygen, sulphur or phosphorus atoms, one or more carbonyl groups or derivatives, one or more rings or heterocycles.

Preferably, B corresponds to the formula II presented above where Z is S. Still more preferably, $R_1$ is the divalent radical $(CH_2)_4$.

However, the invention is not limited to this specific form of biotinyl residue and may also extend to the residues whose —S—$(CH_2)_4$— chain may be replaced by an equivalent chain.

It has already been indicated that the surface density of the functional groups at the surface of the microsphere was advantageously between 1 and 50 per square nanometer.

Preferably, the percentage of biotinylated spacer arms grafted on the surface functional groups is between 1 and 50%. Advantageously, the percentage is between 5 and 30%.

The number n can therefore be determined given the diameter of the sphere and is generally between about 0.1 and about 10.

Preferably, among the numerous divalent radicals R which may be suitable for producing the microspheres according to the invention, there may be mentioned the divalent residue:

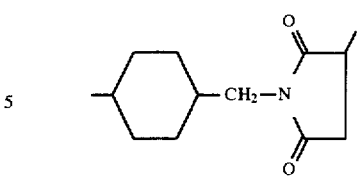

Of course, other equivalent groups may be suitable.

The invention also relates to biotinylated microsphere-avidin or -streptavidin complexes characterized in that the microsphere is chosen from those which were described above.

It relates more particularly to a microsphere in which each biotinyl residue is conjugated to an avidin or streptavidin.

The invention also relates to a process for the preparation of the microsphere or of the complex as they have just been described above, characterized in that the following steps are carried out:

a) activation of the functional groups, b) grafting of the biotinylated chain whose terminal end is reactive towards the activated functional group, c) optionally, complexing with avidin or streptavidin.

Preferably, in order to carry out step c) so as to obtain the biotinylated microsphere-avidin or -streptavidin complex, a molar excess of avidin or of streptavidin will be used per mole of biotin (advantageously in the vicinity of 2).

The coupling (complexing) is carried out in a known manner, for example in the presence of a phosphate buffer+ bovine serum albumin, followed by washing with a phosphate buffer.

Two specific embodiments are now described which allow the respective preparation of the microspheres of structure III and IV.

According to one process for the preparation of the biotinylated microspheres of structure III, the first step consists in activating the carboxylic latex by synthesizing an active ester of sulpho-N-hydroxy-succinimide (S—NHS) in the presence of carbodiimide, especially CMC or 1-cyclohexyl-3-(2-morpholinoethyl)carbodiimide metho-p-toluenesulphonate or EDC (1-ethyl-3-(3-dimethylaminopropylcarbodiimide methiodide) according to the following reaction:

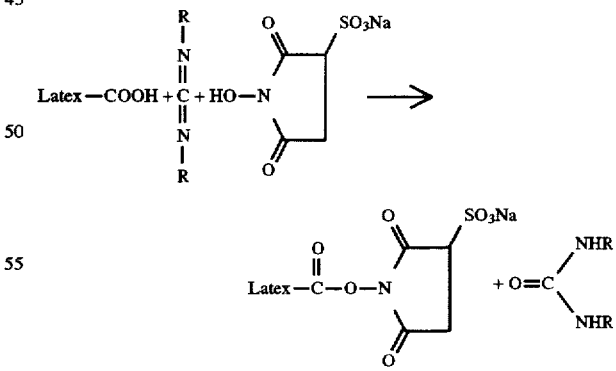

The reaction is carried out in aqueous solution. The reaction of the carbodiimide with the carboxylic latexes in pure water is practically instant provided that the carbodiimide is used in excess.

According to a preferred embodiment, an aqueous solution of S—NHS is added immediately after the carbodiimide. The reaction may be controlled by monitoring the disappearance of S—NHS by visible UV absorption spectrometry (λ max=268 nm; molar extinction coefficient: ε=7500 mol$^{-1}$0.1 .cm$^{-1}$ in phosphate buffer pH=7).

For this activated ester preparation step, it is preferable, in order to obtain a rapid reaction and one which is as complete as possible, to work with a molar excess of EDC especially of between 2 and 20, preferably of between 4 and 10 (in relation to the —COOH functional groups of the latex) and a molar excess of S—NHS especially greater than the concentration of EDC, that is to say between 5 and 100 (in relation to the —COOH functional groups of the latex), preferably between 7 and 50 for a period of activation of 15 to 20 minutes. The excess of S—NHS is removed by several washes with water or with an aqueous NaCl solution (for example 0.25M) until the supernatant has a negligible OD.

The second step consists in the grafting of the biotinylated chain with an amine terminus to the activated latex by formation of an amide bond according to the following reaction:

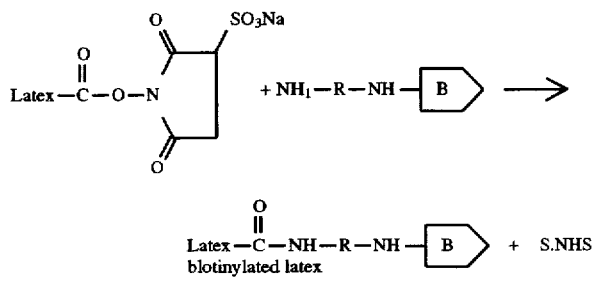

Preferably, the reaction is carried out so that there is a substantially stoichiometric proportion of biotinylated chain in relation to the number of —COOH functional groups present on the microsphere. The grafting of an amine on the activated latex may be controlled by assaying of the S—NHS released during the transamidation reaction. The reaction is carried out in a buffer with a basic pH, especially in the vicinity of 9, especially a borax buffer, but can also be carried out in water or in an aqueous NaCl solution.

The process for the preparation of the biotin-divalent chain compounds is carried out by synthesis routes which are known to persons skilled in the art, starting with commercially available diamines, of which one NH$_2$ radical is optionally masked.

One process for the preparation of a microsphere of structure IV is characterized in that it comprises:

a) the activation of the amine-containing latex with a heterobifunctional spacer arm of the sulphosuccinimidyl-4-(N-maleimidoalkyl)aryl ester type such as sulphosuccinimidyl-4-(N-maleimidomethyl)cyclohexane-1-carboxylate or S—SMCC, or the maleimidosulphosuccinimidyl ester of caproic acid, b) the grafting of the biotinylated chain with an —SH terminus onto the activated latex.

The activation of the amine-containing latex is performed for example under the action of sulphosuccinimidyl-4-(N-maleimidomethyl)cyclohexane-1-carboxylate or S—SMCC, of formula:

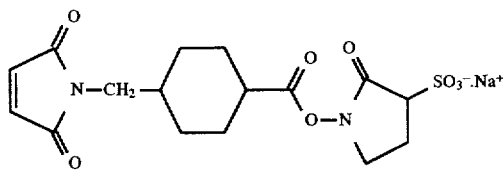

at a neutral or a slightly basic pH. The reaction between the amine-containing latex and the S—SMCC is monitored by UV spectrophotometry. On the centrifuged samples, 1 peak at 268 nm, due to the appearance of S—NHS, can be detected.

The reaction with the biotinylated spacer arm with a sulphydryl terminus consists in the following reaction:

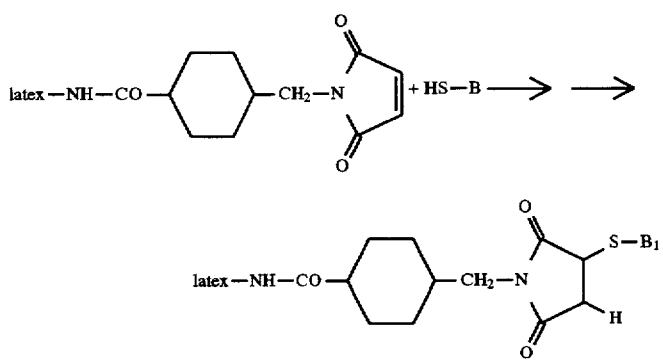

The subject of the invention is finally the use of the microspheres or of the complexes described above as diagnostic or detection agent.

The avidin- or streptavidin-biotin systems can be used in a wide variety of biological fields. The complexes or microspheres described above can especially be used in nucleic acid hybridization, immunological assay or enzymatic assay tests.

According to a first feature, the microspheres can be used in the fields of DNA separation.

In this variant, the microsphere is placed in the presence of avidin or of streptavidin or of the biotinylated DNA strand. This method has the advantage of being able to take advantage of the multiple binding sites of the avidin or the streptavidin with the biotin.

The preparation of the biotinylated DNA is carried out in a known manner by amplification by the PCR method, using an appropriate proportion of biotinylated nucleotides.

It is also possible to apply the same method to the immunological detection by using, in place of the biotinylated DNA, a protein bound to a biotinylated antibody specific for the latter.

This system is of course applicable to other molecules such as lectin, protein A and the like.

According to a second feature, the complexes are directly involved in the above reactions, the avidin or the streptavidin no longer being in a free form.

According to a third feature, the complexes are used as avidin- or streptavidin-biotin affinity support.

The immobilized complexes can be used to purify, recover or characterize the biological species mentioned in the above variant.

For example, a protein present in cells may react with a biotinylated antibody, it being possible for this protein to be subsequently recovered after lysing the cells on the affinity column formed by the complex according to the invention.

The elution may be provided by dissociation of the protein from the complex.

Likewise, a radioactive DNA probe attached to a DNA previously amplified by PCR and biotinylated can be immobilized on such a support consisting of the complexes according to the invention. Radioactive counting indicates the number of DNA molecules to be detected.

Other applications comprise especially the solid phase sequencing of DNA in combination with the PCR method, cell sorting in combination with antibodies specific for the cell considered and biotinylated (cf. Clin. Chem. 37/5, 625–636 (1991) P. Diamandis et al.).

Of course, other applications may be envisaged by persons skilled in the art without leaving the framework of the present invention.

The examples below illustrate the present invention.

EXAMPLE 1

Preparation of the biotinylated magnetic latex

The magnetic latex used is that marketed by the company PROLABO under the reference ESTAPOR M1. 070/60 which has the following characteristics:

| | |
|---|---|
| mean diameter of a bead | 0.8 µm |
| estimated density | 1.94 g · ml$^{-1}$ |
| percentage mass of latex in suspension | 10% |
| percentage mass of ferrite (magnetic pigment) | 60% |
| surface concentration of the —COOH functional groups | 197 µeq · g$^{-1}$ of dry latex |
| surface area of a bead | 2 µm$^2$ |
| volume of a bead | 0.27 µm$^3$ |
| number of beads/g of dry latex | 2 × 10$^{12}$ |
| number of —COOH functional groups/bead | 6.21 × 10$^6$ |
| density of the —COOH functional groups | 31 —COOH/nm$^2$ |

These latexes are polydisperse.

The latex is washed prior to the activation.

24 mg of washed microbeads are introduced into 1 ml of double-distilled water, with stirring (Vortex 400 rpm), which gives a concentration of carboxylic functional group of 474 µM. An EDC (1-ethyl-3-(3-dimethylaminopropylcarbodiimide methiodide) molar excess of 5 is added and an S—NHS molar excess of 50 is added 1 minute after the EDC.

Within fifteen minutes, the quantity of S—NHS necessary for the formation of active ester is completely consumed. The excess S—NHS is removed by several washes with a 0.25M aqueous NaCl solution, until the supernatant has a negligible OD.

The grafting of the biotin-X-cadaverine was performed under the following conditions:

medium: distilled water (4 ml), biotin-X-cadaverine in stoichiometric quantity in relation to the initial —COOH functional groups, vortex stirring (400 revolutions/min).

The product obtained has the following characteristics:

The percentage of latex grafted by the biotin-X-cadaverine is about 7% (expressed as microequivalents of biotin functional groups in relation to the initial carboxylic functional groups).

A streptavidin peroxidase solution in double-distilled water containing 0.01% sodium azide (final concentration) is added to the biotinylated latex in an amount of 2 moles of streptavidin peroxidase per mole of biotin grafted on latex, that is to say 1 mg of streptavidin coupled to peroxidase for 2.1 µg of biotin.

The biotin-streptavidin coupling is carried out in PBS+ BSA buffer (0.1M phosphate, pH 7.2 in 0.25M NaCl containing 1 g/l of BSA (bovine serum albumin)), then the latex-streptavidin is washed four times with 0.1M phosphate buffer in 0.25M NaCl and stored in 1 ml of this buffer.

EXAMPLE 2

Preparation of biotinylated nonmagnetic carboxylic latex

The nonmagnetic latex used is that marketed by the company PROLABO under the reference ESTAPOR K1. 030 and has the following characteristics:

| | |
|---|---|
| mean diameter of a bead | 0.3 µm |
| estimated density | 1 g · ml$^{-1}$ |
| percentage mass of latex in suspension | 10% |
| surface concentration of the —COOH functional groups | 237 µeq · g$^{-1}$ of dry latex |
| surface area of a bead | 0.28 µm$^2$ |
| volume of a bead | 0.0139 µm$^3$ |
| number of beads/g of dry latex | 7.9–10$^{13}$ |
| number of —COOH functional groups/bead | 2 × 10$^6$ |
| density of the —COOH functional groups | 7.1 —COOH/nm$^2$ |

These latexes are monodisperse.

The latex is washed prior to the activation.

The activation reaction is performed entirely in double-distilled water with a concentration of carboxylic functional group of 62 µM, an EDC excess of 7 and an S—NHS excess of 3, added 1 minute after EDC.

Within three minutes, the quantity of S—NHS necessary for the formation of active ester is completely consumed (OD=0.68).

The grafting of the biotin-X-cadaverine was performed under the following conditions:

medium: distilled water, biotin-X-cadaverine in stoichiometric quantity in relation to the initial —COOH functional groups, vortex stirring (400 revolutions/min).

The percentage of latex grafted by the biotin-X-cadaverine is about 7% (expressed as microequivalents of biotin functional groups in relation to the initial carboxylic functional groups).

A streptavidin peroxidase solution in double-distilled water containing 0.01% sodium azide (final concentration) is added to the biotinylated latex in an amount of 2 moles of streptavidin peroxidase per mole of biotin grafted on latex in order to obtain the complex.

What is claimed is:

1. Latex microsphere comprised of polymers obtained by polymerization of ethylenically unsaturated monomers, having functional groups at the surface, wherein biotinyl residues are grafted onto at least part of said groups, via a divalent chain, and wherein said latex microsphere has the following structure:

$$M-[CO-NH-R-NH-B]_n \qquad III$$

in which:

—CO—NH—R—NH— is said divalent chain, n represents the mean number of molecules grafted per unit of surface area, M represents the latex microsphere, B is a biotinyl residue, R is an optionally substituted divalent hydrocarbon radical optionally containing one or more heteroatoms chosen from the nitrogen, oxygen, sulphur or phosphorus atoms, one or more carbonyl groups or derivatives selected from the group consisting of imine and oxime, one or more rings or heterocycles.

2. Latex microsphere according to claim 1, characterized in that R is a divalent residue of formula:

$$-R_2-\underset{\underset{O}{\|}}{C}-NH-R_3-$$

in which each of $R_2$ and $R_3$, which are identical or different, is a divalent $C_2$–$C_6$ chain.

3. Latex microsphere according to claim 1, characterized in that the biotinyl residue is of formula:

II in which:

$R_1$ is a divalent $C_1$–$C_8$ hydrocarbon radical,

X is either an oxygen atom, a sulphur atom or an imino radical N—H,

Z is a group C=O or —S—.

4. Latex microsphere according to claim 3, characterized in that the biotinyl residue is of formula:

5. Latex microsphere comprised of polymers obtained by polymerization of ethylenically unsaturated monomers, having functional groups at the surface, wherein biotinyl residues are grafted onto at least part of said groups, via a divalent chain, and wherein said latex microsphere has the following structure:

$$M-[NH-CO-R-B]_n \qquad IV$$

in which:

—NH—CO—R— is said divalent chain, n represents the mean number of molecules grafted per unit of surface area, M represents the latex microsphere, B is a biotinyl residue, R is an optionally substituted divalent hydrocarbon radical optionally containing one or more heteroatoms chosen from the nitrogen, oxygen, sulphur or phosphorus atoms, one or more carbonyl groups or derivatives selected from the group consisting of imine and oxime, one or more rings or heterocycles.

6. Latex microsphere according to claim 5, characterized in that R is the divalent residue of formula:

7. Latex microsphere according to claim 5, characterized in that the biotinyl residue is of formula:

II in which:

$R_1$ is a divalent $C_1$–$C_8$ hydrocarbon radical,

X is either an oxygen atom, a sulphur atom or an imino radical N—H,

Z is a group C=O or —S—.

8. Latex microsphere according to claim 7, characterized in that the biotinyl residue is of formula:

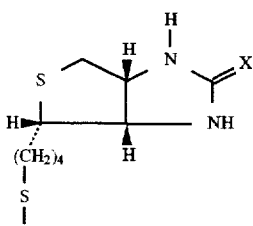

9. Latex microsphere according to claim 1, characterized in that the divalent chain has a mean length ranging from 5 to 120 Å.

10. Latex microsphere according to claim 1 characterized in that the divalent chain has from 3 to 80 atoms.

11. Latex microsphere according to claim 1, characterized in that the surface density of functional groups per square nanometer of microsphere is between 1 and 50.

12. Latex microsphere according to claim 1, characterized in that the percentage of biotinyl residues in relation to the number of functional groups present on the microsphere is between 1 and 50%.

13. Latex microsphere of claim 1 wherein n is between 0.1 and 10 per square nanometer.

14. Complex of a biotinylated latex microsphere with avidin or streptavidin, characterized in that the biotinylated latex microsphere is the microsphere of claim 1.

15. Complex of a biotinylated latex microsphere with avidin or streptavidin according to claim 1, characterized in that about one molecule of avidin or streptavidin is attached per biotinyl residue.

16. Process for the preparation of the microsphere of claim 1 characterized in that the steps are:

a) activation of the functional groups of the microsphere,
  b) grafting of the biotinylated chain whose terminal end is reactive towards the activated functional group, and
  c) optionally, complexing with avidin or streptavidin.

17. Process according to claim 16, characterized in that it comprises:

a) activation the carboxylic latex functional groups by sulpho-N-hydroxysuccinimide in the presence of a carbodiimide, and
  b) grafting of the biotinylated chain with an NH$_2$ terminus onto the activated latex.

18. Process according to claim 8 characterized in that the complex with avidin or streptavidin is obtained by contacting with a molar excess of avidin or streptavidin.

19. Latex microsphere according to claim 5, characterized in that the divalent chain has a mean length ranging from 5 to 120 Å.

20. Latex microsphere according to claim 5, characterized in that the divalent chain has from 3 to 80 atoms.

21. Latex microsphere according to claim 5, characterized in that the surface density of functional groups per square nanometer of microsphere is between 1 and 50.

22. Latex microsphere according to claim 5, characterized in that the percentage of biotinyl residues in relation to the number of functional groups present on the microsphere is between 1 and 50%.

23. Latex microsphere of claim 5 wherein n is between 0.1 and 10 per square nanometer.

24. Complex of a biotinylated latex microsphere with avidin or streptavidin, characterized in that the biotinylated latex microsphere is in the microsphere of claim 5.

25. Complex of biotinylated latex microsphere and avidin or streptavidin according to claim 24, characterized in that about one molecule of avidin or streptavidin is attached per biotinyl residue.

26. Process for the preparation of the microsphere of claim 5, characterized in that the steps are:

a) activation of the functional groups of the microsphere,
  b) grafting of the biotinylated chain whose terminal end is reactive towards the activated functional group, and
  c) optionally, complexing with avidin or streptavidin.

27. Process according to claim 26, characterized in that it comprises:

a) the activation of amine functional latex group by a heterobifunctional spacer arm of a sulphosuccinimidyl-4-(N-maleimidoalkyl) aryl ester, and
  b) the grafting of the biotinylated chain with an —SH terminus onto the activated latex.

28. Process according to claim 27, characterized in that the spacer arm is sulphosuccinimidyl-4-(N-maleimidoalkyl) cyclohexane-1-carboxylate.

29. Process according to claim 26, characterized in that the complex with avidin or streptavidin is obtained by contacting with a molar excess of avidin or streptavidin.

30. In a method of detecting a biological agent in a sample involving contacting the sample with a substrate for the biological agent, the improvement comprising contacting the sample with the substrate bound to the latex microsphere according to claim 1.

31. Method according to claim 30, for hybridization in sequencing of DNA.

32. Method according to claim 30, for purification of proteins or for cell sorting.

33. In a method of detecting a biological agent in a sample involving contacting the sample with a substrate for the biological agent, the improvement comprising contacting the sample with the substrate bound to the latex microsphere according to claim 5.

34. Use according to claim 33, for hybridization, in sequencing of DNA.

35. Method according to claim 33, for purification of proteins or for cell sorting.

* * * * *